(12) United States Patent
Rubæk et al.

(10) Patent No.: US 11,687,075 B2
(45) Date of Patent: Jun. 27, 2023

(54) REMOTELY OPERATED MOBILE SERVICE ROBOTS

(71) Applicant: UVD Robots ApS, Odense SØ (DK)

(72) Inventors: Thomas Rubæk, Odense (DK); Efraim Vitzrabin, Odense (DK); John Erland Østergaard, Odense (DK); Claus Risager, Odense (DK)

(73) Assignee: UVD Robots ApS, Odense (DK)

( * ) Notice: Subject to any disclaimer, the term of this patent is extended or adjusted under 35 U.S.C. 154(b) by 311 days.

(21) Appl. No.: 16/874,976

(22) Filed: May 15, 2020

(65) Prior Publication Data

US 2021/0356958 A1 Nov. 18, 2021

(51) Int. Cl.
*G05D 1/00* (2006.01)
*A61L 2/10* (2006.01)
*A61L 2/24* (2006.01)
*G01C 21/20* (2006.01)
*G05D 1/02* (2020.01)

(52) U.S. Cl.
CPC .............. *G05D 1/0022* (2013.01); *A61L 2/10* (2013.01); *A61L 2/24* (2013.01); *G01C 21/206* (2013.01); *G05D 1/0246* (2013.01); *A61L 2202/11* (2013.01); *A61L 2202/14* (2013.01); *A61L 2202/16* (2013.01); *A61L 2202/25* (2013.01)

(58) Field of Classification Search
None
See application file for complete search history.

(56) References Cited

U.S. PATENT DOCUMENTS

| 10,406,253 | B2 | 9/2019 | Kreitenberg | |
| 10,500,296 | B2* | 12/2019 | Kreitenberg | A61L 2/26 |
| 2016/0375166 | A1* | 12/2016 | Kreitenberg | A61L 2/24 422/24 |
| 2018/0232134 | A1 | 8/2018 | Ebrahimi Afrouzi | |
| 2018/0299899 | A1* | 10/2018 | Suvarna | H04W 16/20 |
| 2020/0029774 | A1 | 1/2020 | Mellinger, III | |

FOREIGN PATENT DOCUMENTS

| TW | M506608 | | 8/2015 | |
| WO | 2006026436 A2 | | 3/2006 | |
| WO | WO-2006026436 A2 | * | 3/2006 | A47L 9/009 |

OTHER PUBLICATIONS

Extended European Search Report for App. Np. EP20175546.9, dated Nov. 27, 2020, 7 pages.
Taiwanese Office Action and Search Report (including English translation) for App. No. TW109116752, dated Jan. 17, 2021, 5 pages.

* cited by examiner

*Primary Examiner* — Andrew Smyth
(74) *Attorney, Agent, or Firm* — Kevin Roddy; Butzel Long

(57) ABSTRACT

Implementations of the disclosed subject matter provide a mobile robot including a motor to drive a drive system to move the mobile robot in an area, a light source to output ultraviolet (UV) light, at least one sensor, a communications interface to receive at least one signal via a communications network, and a first controller to control the drive system, the light source, the at least one sensor, and the communications interface. Operations of the mobile robot may be controlled based in part on the at least one signal received via the communications network from a second controller that is in a location that is remote from the area where the mobile robot is operating.

14 Claims, 5 Drawing Sheets

REMOTELY OPERATED MOBILE SERVICE ROBOTS

BACKGROUND

Mobile devices, such as mobile robots, can be operated so as to disinfect indoor areas, such as a room that has surfaces contaminated with bacteria, viruses, or other pathogens. Typically, such devices do not provide additional services to people who operate within such areas.

BRIEF SUMMARY

According to an implementation of the disclosed subject matter, a device including a mobile robot may have a motor to drive a drive system to move the mobile robot in an area, a light source to output ultraviolet (UV) light, at least one sensor, a communications interface to receive at least one signal via a communications network, and a first controller to control the drive system, the light source, the at least one sensor, and the communications interface. Operations of the mobile robot may be controlled based in part on the at least one signal received via the communications network from a second controller that is in a location that is remote from the area where the mobile robot is operating.

Additional features, advantages, and implementations of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

Figure 1:
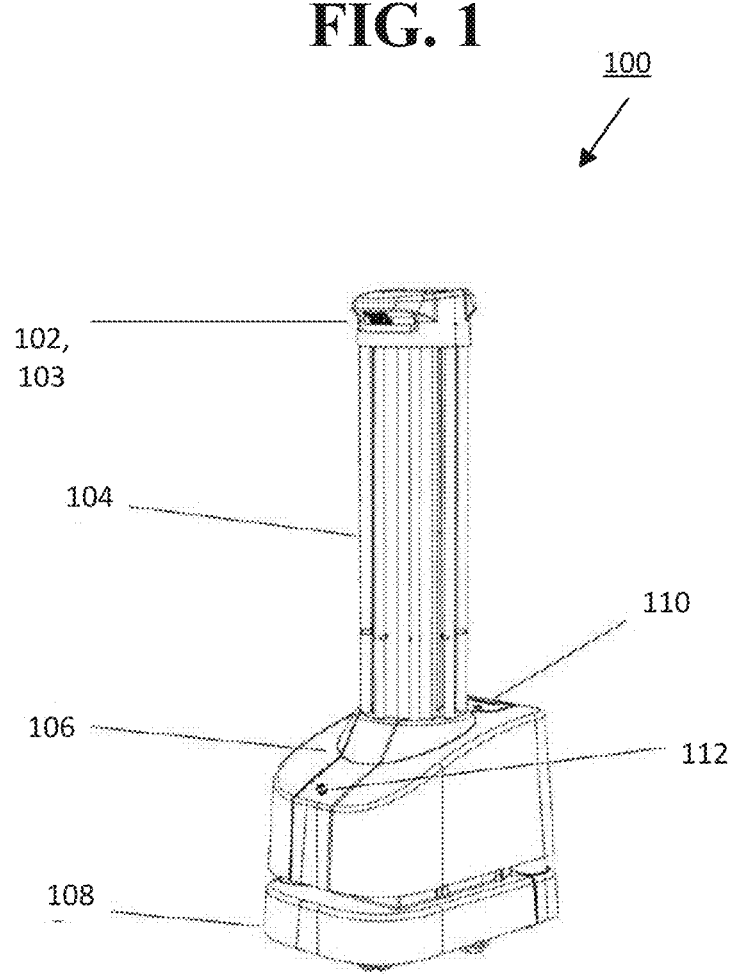
FIGS. 1-3 show a plurality of external views of a mobile robot having sensors to detect surfaces and objects in an area, and a light source to output UV light according to implementations of the disclosed subject matter.

Implementations of the disclosed subject matter provide a mobile robot with a light source which may output ultraviolet (UV) light to disinfect a predetermined area. The mobile robot may be used as part of a regular cleaning cycle of an indoor area (e.g., a room, building, airplane, school, or the like) and/or an outdoor area, and may prevent and/or reduce the spread of infectious diseases, viruses, bacteria, and other types of harmful organic microorganisms in the environment by breaking down their DNA-structure with UV light. The mobile robot may include at least one sensor to detect objects, surfaces, and/or whether humans are within the area. The mobile robot may include a microphone to detect sound within the area, and may include a speaker to output notifications (e.g., mobile robot operational status, disinfection operation status, and the like), instructions, or the like. The operation of the mobile robot may be controlled by a first controller included with the mobile robot, and/or may be controlled by a remotely-located second controller that is communicatively coupled to the mobile robot. The second controller may be operated by a user based on signals transmitted from the mobile robot that include sensor signals (e.g., which may include images and/or video), microphone signals, and the like. The user of the second controller may access and/or operate the functions of the mobile robot via a communications network, which may include local access points to the area and/or the mobile robot, and/or remote access points.

The second controller may receive signals from the at least one sensor and/or microphone of the mobile robot, and may determine whether there is a human within the area. When it is determined that a human is not present within the area, the second controller may control the operation of the light source of the mobile robot to output UV light to disinfect the area.

When the mobile robot includes a microphone, sound received by the microphone may be transmitted to the second controller via a signal, and the user of the second controller may hear any sounds near the mobile robot. For example, if the user hears sounds that may be from a human, the user of the second controller may control the light source of the mobile robot to stop outputting UV light.

If there is at least one speaker on the robot, the user can provide signals from the second controller to the mobile robot to be output on the speaker, where the signals may include notifications, instructions, alerts, or the like. In some implementations, the second controller may include a microphone, and the user's speech received by the microphone may be transmitted as a signal to the mobile robot, which may output the signal via the speaker. In some implementations, the user of the second controller may provide instructions for use, operation, repair, or the like to one or more persons near the speaker of the mobile robot.

In some implementations, the mobile robot and/or the second controller may map the area. The at least one sensor of the mobile robot may detect surfaces, objects, and the like that may be within the area, and the mobile robot and/or the second controller may generate a map of the area based on the signals received from the at least one sensor.

Figure 2:
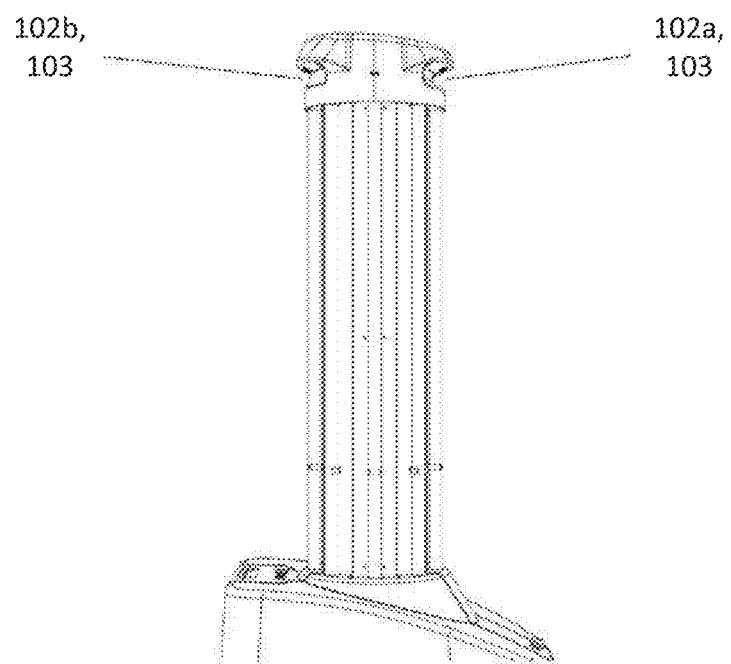
Figure 3:
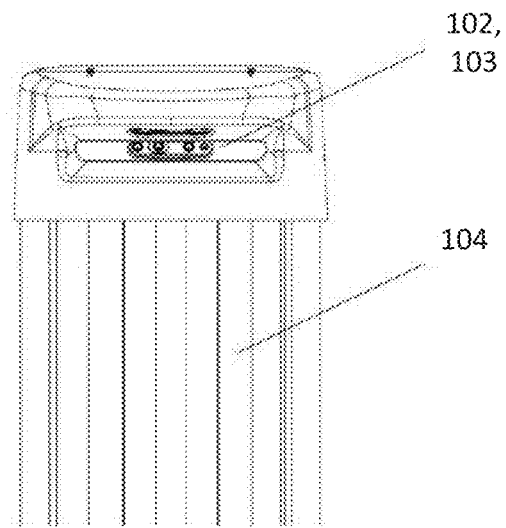
Figure 4:
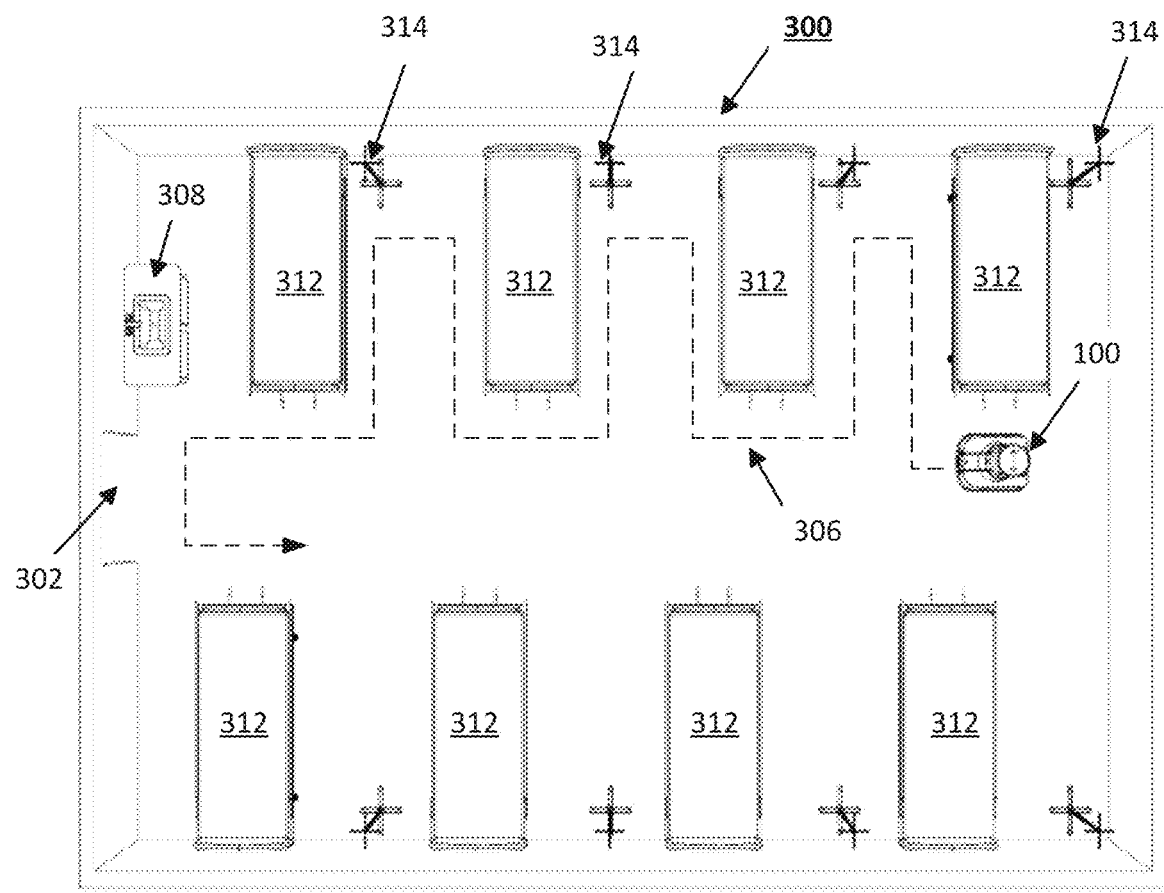
FIG. 4 shows an example of a path of the mobile robot to apply a dosage of UV light in an area according to an implementation of the disclosed subject matter.

FIGS. 1-6 show implementations of the disclosed subject matter that include a mobile robot (e.g., mobile robot 100 shown in FIGS. 1-6) having a motor to drive a drive system (e.g., drive system 108 shown in FIG. 5) to move the mobile robot in an area (e.g., area 300 shown in FIG. 4). The mobile robot may include a light source (e.g., light source 104 shown in FIGS. 1, 3, and 5) to output ultraviolet (UV) light. The mobile robot may include at least one sensor (e.g., sensor 102, 102a, 102b, 106 shown in FIGS. 1-3 and 5).

Figure 5:
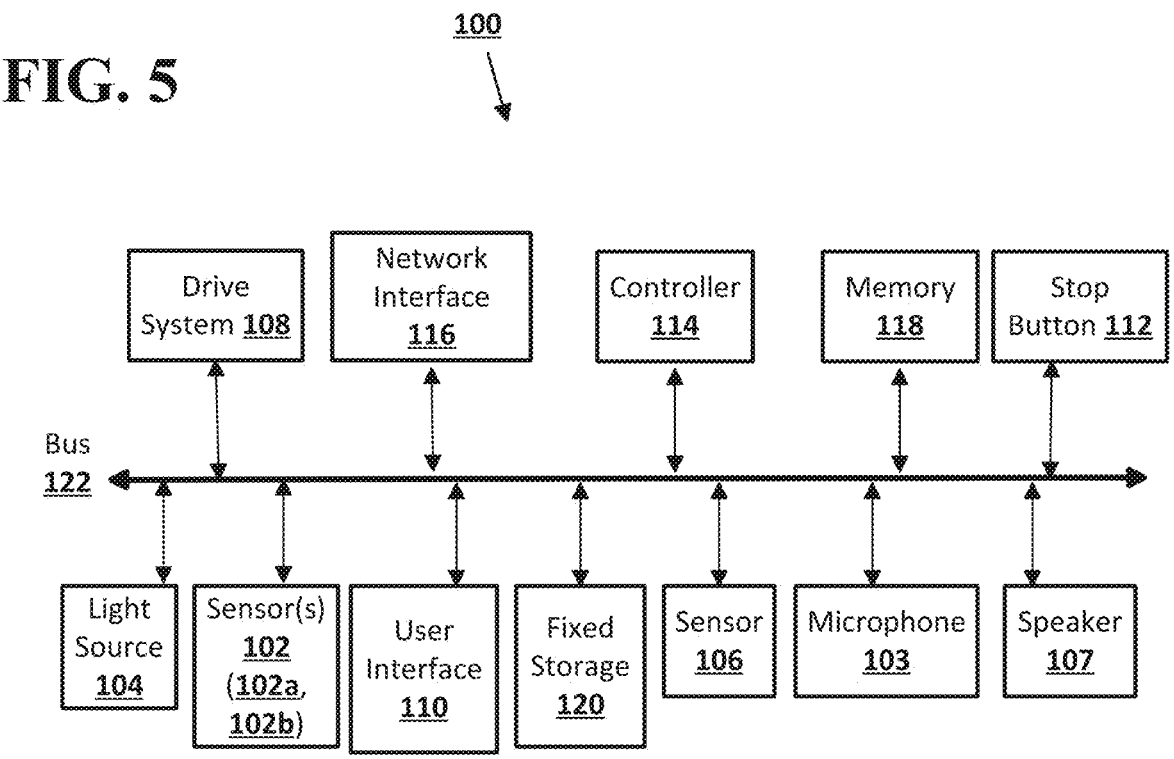
FIG. 5 shows an example configuration of the mobile robot of FIGS. 1-4 according to an implementation of the disclosed subject matter.
Figure 6:
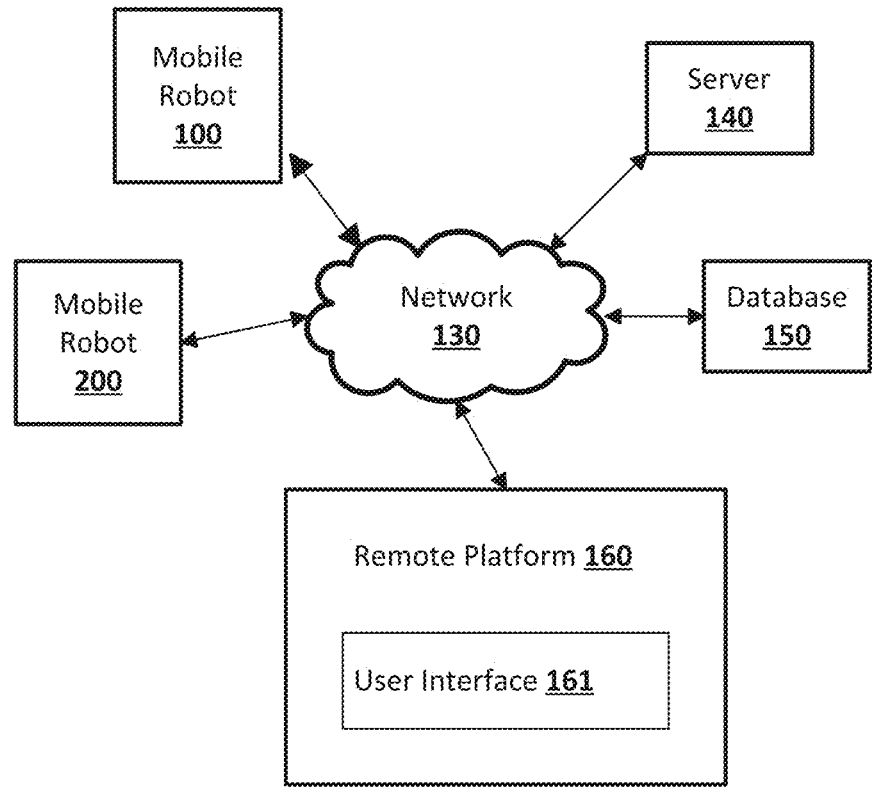
FIG. 6 shows a network configuration which may include a remote platform with an interface to control one or more mobile robots in a remote location according to implementations of the disclosed subject matter.

The mobile robot may include a communications interface (e.g., network interface 116 shown in FIG. 5) to receive at least one signal via a communications network (e.g., network 130 shown in FIG. 6). A first controller (e.g., controller 114 shown in FIG. 5) may control the drive system (e.g., drive system 108 shown in FIG. 5), the light source (e.g., light source 104 shown in FIGS. 1, 3, and 5), the at least one sensor (e.g., sensor 102, 102a, 102b, 106 shown in FIGS. 1-3 and 5), and/or the communications interface (e.g., network interface 116 shown in FIG. 5) of the mobile robot. Operations of the mobile robot may be controlled based in part on the at least one signal received via the communications network (e.g., network 130 shown in FIG. 6) from a second controller (e.g., server 140 and/or remote platform 160 shown in FIG. 6) that is in a location that is remote from the area (e.g., area 300 shown in FIG. 4) where the mobile robot is operating.

The second controller may include a user interface (e.g., user interface 161 shown in FIG. 6) to display at least one image captured by the at least one sensor that is transmitted to the second controller by the communications interface via the communications network. The user may control the movement and/or other operations of the mobile robot based on images, video, and/or other sensor data that is transmitted from the mobile robot to the second controller. For example, the user may control the mobile robot to move about the area and disinfect the area by outputting UV light when no humans are detected by the sensors to be within the area. In some implementations, the second controller may include a microphone, and the user's speech received by the microphone may be transmitted as a signal to the mobile robot, which may output the signal via the speaker. The user of the second controller may provide instructions for use, operation, repair, or the like to one or more persons near the speaker of the mobile robot.

In some implementations, the mobile robot may include at least one microphone (e.g., microphone 103 shown in FIGS. 1-3 and 5), communicatively coupled to a first controller (e.g., controller 114 shown in FIG. 5), to capture sound in the area (e.g., area 300 shown in FIG. 4). The communications interface may transmit a signal that includes the captured sound to the second controller (e.g., server 140 and/or remote platform 160 shown in FIG. 5). The at least one signal received by the mobile robot to control the operations of the mobile robot may be based on the signal that includes the captured sound. That is, the captured sound may be transmitted to the second controller, and the second controller may control the mobile robot based on the captured sound using a control signal. For example, the sound transmitted from the mobile robot to the second controller may be used to determine whether there is a human or not within the area. If a human is determined to be within the area, the user of the second controller may stop the output of UV light from the light source of the robot. In another example, the user of the second controller may provide instructions, notifications, and the like to the one or more people that are determined to be near the mobile robot based on the sound received by the microphone.

The mobile robot may include at least one speaker (e.g., speaker 107 shown in FIG. 5), communicatively coupled to the first controller (e.g., controller 114 shown in FIG. 5), to output a notification based on the at least one signal received from the second controller (e.g., server 140 and/or remote platform 160 shown in FIG. 5). The at least one speaker may output a notification (e.g., a status notification, such as a status of disinfection of the area, an operational status of the mobile robot, or the like), instructions to operate the mobile robot, instructions to install the mobile robot within the area, a notification or instructions to provide maintenance to the mobile robot, a notification or instructions to troubleshoot an operational problem with the mobile robot, and a notification for an operational incident of the mobile robot that are included with the at least one signal received at the communications interface via the communications network.

The communications interface of the mobile robot may transmit at least one output signal, which may include output signals of the at least one sensor, a generated map of the area, and/or an operational state of the mobile robot based on a request included in the at least one signal received by the communications interface.

In some implementations, the second controller (e.g., server 140 and/or remote platform 160 shown in FIG. 5) may determines whether a human is within the area (e.g., area 300 shown in FIG. 4) based on an output signal received via the communications network from the mobile robot. The second controller may transmit a control signal to the mobile robot to control the light source to output UV light when it is determined that the human is not within the area. That is, when it is determined that the human is not within the area (e.g., based on signals from the sensors 102, 106 and/or the microphone 103), the second controller may control the light source 104 to output UV light to disinfect the area. If a human is determined to be within the area, the controller may prohibit the light source from outputting UV light so as to prevent the human from being harmed.

In some implementations, the communication interface of the mobile robot may output a notification signal to the second controller. The notification signal may be output when the mobile robot is unable to move because of an obstacle (e.g., an object, a surface, and/or other inanimate object) in the area, the mobile robot receives a selection from a user interface to request assistance, the area is different from a map of the area used to move the mobile robot within the area, and/or when the mobile robot is unable to determine its location within the area.

In some implementations, the first controller and/or the second controller may generate a map based on objects and/or surfaces detected by the at least one sensor as the mobile robot moves within the area. At least one of the first controller, and the second controller annotates the objects on the generated map. The generated map may include rooms, doors, beds, chairs, tables, equipment, stairs, elevators, objects, and the like in the area that are detected by the at least one sensor of the mobile robot.

In some implementations, the second controller may control the mobile robot using the at least one signal to perform at least one of deploying the mobile robot in the area, installing the robot in the area, disinfecting the area by outputting the UV light, and/or controlling the mobile robot to handle an operation incident.

The mobile robot arrangement that may be remotely controlled by a user of the second controller as described throughout may be used, for example, when installing the mobile robot in a hospital, care facility, store, warehouse, manufacturing facility, office building or other work environment, performance space, museum, public facility, airplane or other transport vehicle, or other setting. In this example, technical staff may unpackage the mobile robot and may activates it for operation in at least one area of the hospital, care facility, store, warehouse, manufacturing facility, office building or other work environment, performance space, museum, public facility, airplane or other transport vehicle, or other setting. The user of the second controller may communicatively connect the second controller to the mobile robot to perform initialization and/or installation operations of the mobile robot.

In another example, the mobile robot and the second controller may be used to map the hospital, care facility, store, warehouse, manufacturing facility, office building or other work environment, or other setting. The at least one sensor of the mobile robot may be used to detect object, surfaces, features, and the like as the mobile robot moves about the area and may generate a map of the area. In some implementations, the mobile robot and the second controller may be used to generate the map. The user of the second controller may annotate one or more objects, such as rooms, doors, elevators, stairs, restricted access zones, and the like on the generated map.

In another example, the mobile robot and the second controller may be used to train one or more users of the mobile robot. Instructions for operating the robot may be provided by the second controller and may be output by the speaker of the mobile robot. In some implementations, a third controller communicatively coupled to the mobile robot, and the user of the second controller may guide and/or assist the user to be trained at the third controller with the operation of the mobile robot. For example, the user of the second controller may guide the user of the third controller in controlling the mobile robot to disinfect a portion of an area using UV light.

In a further example, rather than have a user touch the mobile robot (e.g., to avoid the spread of germs, viruses, or the like) to make selections (e.g., from user interface 110 shown in FIG. 5) regarding its operation, a user may communicatively connect with the mobile robot via a communications network from the second controller to control the operation of the mobile robot. In some implementations, the user may control (e.g., manually control) the mobile robot via the second controller to control the movement of the mobile robot within an area, and/or may control the light source of the mobile robot to output UV light to disinfect the area. The user may control the movement of the mobile robot so as to guide the mobile robot between obstacles, such as those detected by the at least one sensor of the mobile robot.

In another example, when the mobile robot is operating autonomously and becomes stuck (e.g., it cannot move within the area), the mobile robot may transmit a notification to the second controller, where a user of the second controller may assist the mobile robot in with moving within the area.

In a further example, the mobile robot may be deployed within an area (e.g., hospital, care facility, store, warehouse, manufacturing facility, office building or other work environment, or other setting), and the user of the second controller may operate the robot within the area to provide a disinfection service by controlling the mobile robot.

FIGS. 1-3 show a plurality of external views of a mobile robot 100 that includes sensors to detect surfaces and objects in an area, and a light source to output UV to disinfect the air, objects, and/or surfaces in the area according to implementations of the disclosed subject matter. The mobile robot 100 may include at least a sensor 102 (shown as sensor 102a and 102b in FIG. 2), a light source 104 to output ultraviolet light, at least a sensor 106, a drive system 108, a user interface 110, and/or a stop button 112. A controller (e.g., controller 114 shown in FIG. 5 and described below) may be communicatively coupled to the at least one first sensor 102, the light source 104, the at least one second sensor 106, the drive system 108, the user interface 110 and the stop button 112, may control the operations of the mobile robot 100. In some implementations, the mobile robot may be controlled by the remote platform 160 via the network 130, as shown in FIG. 6.

The at least one first sensor 102 (including sensors 102a, 102b shown in FIG. 2) may determine at least one of an orientation of the mobile robot 100 (e.g., a direction that a front side and/or a first side of a robot is facing), a location of the mobile robot 100 (e.g., a location of the mobile robot 100 in an area), and/or when the light source 104 is within a predetermined distance of a surface and/or object in the area. In some implementations, the first sensor 102 may detect air, a surface, and/or objects that may disinfected with UV light from the light source 104.

In some implementations, the at least one first sensor 102 may have a field of view of 70 degrees diagonally. The at least one sensor 102 may have a detection distance of 0.2-4 meters. As shown in FIGS. 1-3, the at least one first sensor 102 may be disposed over the light source 104.

The at least one first sensor 102 may include a first side sensor disposed on a first side of the mobile robot 100 and a second side sensor that may be disposed on a second side of the device. For example, as shown in FIG. 2, sensor 102a may be disposed on a first side (e.g., a front side) of the mobile robot 100, and sensor 102b may be disposed on a second side (e.g., a back side) of the mobile robot 100. Although sensors on two sides of the robot are shown in FIG. 2, there may be a plurality of sensors disposed on different sides of the mobile robot 102 to at least detect surfaces and/or objects. In some implementations, sensor 102a and/or sensor 102b may be disposed over the light source 104.

The light source 104 may be one or more bulbs, one or more lamps, and/or an array of light emitting diodes (LEDs) or organic light emitting diodes (OLEDs) to emit UV light (e.g., light having a wavelength of 10 nm-400 nm). The dosage of the UV light (e.g., intensity, duration, optical power output, or the like) may be controlled by the controller 114, which may also turn on or off a portion or all of the devices (e.g., bulbs, lamps, LEDs, OLEDs) of the light source 104. The light source may be controlled to emit UV light when the mobile robot is within an area, as the mobile robot moves within the area, before the mapping of the area, during the mapping of the area, and/or after the mapping of the area.

The sensor 106 may be communicatively coupled to the controller 114 shown in FIG. 5, and may be used to detect air, surfaces, and/or objects that may be mapped and/or disinfected with UV light from the light source 104. In some implementations, the sensor 106 may determine at least one of an orientation of the mobile robot 100 (e.g., a direction that a front side and/or a first side of a robot is facing), a location of the mobile robot 100 (e.g., a location of the mobile robot 100 in an area), and/or when the light source 104 is within a predetermined distance of a surface and/or object in the area (e.g., sink 308, bed 312, 4-hook IV stand 314, or the like of area 300 shown in FIG. 4).

In some implementations, the sensor 102, 106 may be an image sensor, a thermal sensor, a time-of-flight sensor, an ultrasonic sensor, a two-dimensional (2D) Light Detection and Ranging (LiDAR) sensor, a three-dimensional (3D) LiDAR sensor, and/or a radar (radio detection and ranging) sensor, a stereo vision sensor, 3D three camera, a structured light camera, or the like. The sensor 106 may have a field of view of 20-27 degrees. In some implementations, the sensor 106 may have a detection distance of 0.05-4 meters.

The mobile robot 100 may include a motor to drive the drive system 108 to move the mobile robot in an area, such as a room, a building, or the like. The drive system 108 may include wheels, which may be adjustable so that the drive system 108 may control the direction of the mobile robot 100.

In some implementations, the mobile robot 100 may include a base with the drive system 108, and the sensor 102, 106 may be disposed on the base.

The controller 114 may control and/or operate the mobile robot 100 in an operation mode which may be a manual mode, an autonomous mode, and/or a tele-operation mode. In the manual mode, the controller 114 may receive on or more control signals from the user interface 110 and/or the stop button 112. For example, a user may control the movement, direction, and/or stop the motion of the mobile robot 100 by making one or more selections on the user interface 110. The stop button 112 may be an emergency stop (ESTOP) button which may stop all operations and/or movement of the mobile robot 100 when selected. In some implementations, the controller 114 may receive at least one control signal via a network interface 116 (shown in FIG. 5) when operating when operating in the tele-operation mode. For example, the network interface may receive control signals via network 130 from server 140, and/or remote platform 160, as described below in connection with FIG. 6.

In some implementations, when the mobile robot 100 is moving in a direction, the sensor 102, 106 may detect a geometry of one or more surfaces and/or objects (e.g., sink 308, bed 312, 4-hook IV stand 314, and/or other objects and/or surfaces of area 300 shown in FIG. 4). The output of the at least one first sensor 102 may be, for example, a point cloud of the one or more objects in the path of the mobile robot 100. When the sensor 102 and/or sensor 106 is a stereo vision sensor, images from two sensors (i.e., where the two sensors may be part of the stereo vision sensor of the sensor 102 and/or sensor 106) within a known distance from one another distance may be captured at a predetermined point in time, and/or at predetermined time intervals with a global shutter. The global shutter may be configured so that the two sensors of the stereo vision sensor may capture images about simultaneously. One or more features may be determined from the captured images, and be compared to one another to determine portions that are matching. As the focal length of the two sensors of the stereo vision sensor and the distance between the two sensors (e.g., about 6 cm) may be stored in memory 118 and/or fixed storage 120 (shown in FIG. 5), the controller 114 and/or the at least one first sensor 102 may use the captured images and the stored values to determine the distance from the sensor 102, 106 to the surfaces and/or objects, and may be used by the processor for outputting UV light from the light source. In some implementations, the sensor 102, 106 may include at least one laser, LED, and/or OLED, to radiate one or more points on surfaces of objects, when the objects may be without identifying features (e.g., blank walls).

When detecting the surface and/or object, the sensor 102, 106 may be a time-of-flight (TOF) sensor. At least one photon of light may be output by the sensor 102, 106, and may be transmitted through the air. When the at least one photon of light radiates on a surface and/or an object, a portion of the light may be reflected by the surface and/or the object may return to a receiver portion of the sensor 102, 106. The sensor 106 may calculate the time between sending the at least one photon of light and receiving the reflection, and multiply this value by the speed of light in air, to determine the distance between the sensor 102, 106 and surface and/or object. This may be used to generate the map of the area that the mobile robot is operating within.

FIG. 5 shows example components of the mobile robot 100 suitable for providing the implementations of the disclosed subject matter. The mobile robot 100 may include a bus 122 which interconnects major components of the mobile robot 100, such as the drive system 108, a network interface 116 operable to communicate with one or more remote devices via a suitable network connection, the controller 114, a memory 118 such as Random Access Memory (RAM), Read Only Memory (ROM), flash RAM, or the like, the stop button 112, the light source 104, the at least one first sensor 102, a user interface 110 that may include one or more controllers and associated user input devices such as a keyboard, touch screen, and the like, a fixed storage 120 such as a hard drive, flash storage, and the like, and the sensor 106, a microphone 103, and/or a speaker 107 to output an audio notification and/or other information.

The bus 122 allows data communication between the controller 114 and one or more memory components, which may include RAM, ROM, and other memory, as previously noted. Typically RAM is the main memory into which an operating system and application programs are loaded. A ROM or flash memory component can contain, among other code, the Basic Input-Output system (BIOS) which controls basic hardware operation such as the interaction with peripheral components. Applications resident with the mobile robot 100 are generally stored on and accessed via a computer readable medium (e.g., fixed storage 120), such as a solid state drive, hard disk drive, an optical drive, solid state drive, or other storage medium.

The network interface 116 may provide a direct connection to a remote server (e.g., server 140, database 150, and/or remote platform 160 shown in FIG. 13) via a wired or wireless connection (e.g., network 130 shown in FIG. 13). The network interface 116 may provide such connection using any suitable technique and protocol as will be readily understood by one of skill in the art, including digital cellular telephone, WiFi, Bluetooth®, near-field, and the like. For example, the network interface 116 may allow the mobile robot 100 to communicate with other computers via one or more local, wide-area, or other communication networks, as described in further detail below. The mobile robot may transmit data via the network interface to the remote server that may include a path of operation, the surfaces and/or areas radiated with UV light, and the like.

Many other devices or components (not shown) may be connected in a similar manner. Conversely, all of the components shown in FIG. 5 need not be present to practice the present disclosure. The components can be interconnected in different ways from that shown. Code to implement the present disclosure can be stored in computer-readable storage media such as one or more of the memory 118, fixed storage 120, or on a remote storage location.

FIG. 6 shows an example network arrangement according to an implementation of the disclosed subject matter. Mobile robot 100 described above, and/or a similar mobile robot 200 may connect to other devices via network 130. The network 130 may be a local network, wide-area network, the Internet, or any other suitable communication network or networks, and may be implemented on any suitable platform including wired and/or wireless networks. The mobile robot 100 and/or mobile robot 200 may communicate with one another, and/or may communicate with one or more remote devices, such as server 140, database 150, and/or remote platform 160. The remote devices may be directly accessible by the mobile robot 100, 200 or one or more other devices may provide intermediary access such as where a server 140 provides access to resources stored in a database 150. The mobile robot 100, 200 may access remote platform 160 or services provided by remote platform 160 such as cloud computing arrangements and services. The remote platform 160 may include one or more servers 140 and/or databases 150.

More generally, various implementations of the presently disclosed subject matter may include or be embodied in the form of computer-implemented processes and apparatuses for practicing those processes. Implementations also may be embodied in the form of a computer program product having computer program code containing instructions embodied in non-transitory and/or tangible media, such as solid state drives, DVDs, CD-ROMs, hard drives, USB (universal serial bus) drives, or any other machine readable storage medium, such that when the computer program code is loaded into and executed by a computer, the computer becomes an apparatus for practicing implementations of the disclosed subject matter. Implementations also may be embodied in the form of computer program code, for example, whether stored in a storage medium, loaded into and/or executed by a computer, or transmitted over some transmission medium, such as over electrical wiring or cabling, through fiber optics, or via electromagnetic radiation, such that when the computer program code is loaded into and executed by a computer, the computer becomes an apparatus for practicing implementations of the disclosed subject matter. When implemented on a general-purpose microprocessor, the computer program code segments configure the microprocessor to create specific logic circuits.

In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions. Implementations may include using hardware that has a processor, such as a general purpose microprocessor and/or an Application Specific Integrated Circuit (ASIC) that embodies all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A device comprising:
 a mobile robot including:
  a motor to drive a drive system to move the mobile robot in an area;
  a light source to output ultraviolet (UV) light disposed over the drive system;
  at least one sensor;
  a communications interface to receive at least one signal via a communications network; and
  a first controller to control the drive system, the light source, the at least one sensor, and the communications interface,
 wherein operations of the mobile robot are controlled based in part on the at least one signal received via the communications network from a second controller that is in a location that is remote from the area where the mobile robot is operating, and
 wherein the communication interface is configured to output a notification signal to the second controller when the mobile robot is unable to determine its location within the area.

2. The device of claim 1, wherein the second controller includes a user interface to display at least one image captured by the at least one sensor that is transmitted to the second controller by the communications interface via the communications network.

3. The device of claim 1, wherein the mobile robot further comprises:
 at least one microphone, communicatively coupled to the first controller, to capture sound in the area,
 wherein the communications interface transmits a signal that includes the captured sound to the second controller.

4. The device of claim 3, wherein the at least one signal received by the mobile robot to control the operations of the mobile robot is based on the signal that includes the captured sound.

5. The device of claim 1, wherein the mobile robot further comprises:
 at least one speaker, communicatively coupled to the first controller, to output a notification based on the at least one signal received from the second controller.

6. The device of claim 5, wherein the at least one speaker outputs at least one from the group consisting of: a notification; a status of disinfection of the area; instructions to operate the mobile robot; instructions to install the mobile robot within the area; a notification or instructions to provide maintenance to the mobile robot; a notification or instructions to troubleshoot an operational problem with the mobile robot; and a notification for an operational incident of the mobile robot that are included with the at least one signal received at the communications interface via the communications network.

7. The device of claim 1, wherein the communications interface transmits at least one output signal selected from the group consisting of: output signals of the at least one sensor, a generated map of the area, and an operational state of the mobile robot based on a request included in the at least one signal received by the communications interface.

8. The device of claim 1, wherein the second controller determines whether a human is within the area based on an output signal received via the communications network from the mobile robot, and the second controller transmits a control signal to the mobile robot to control the light source to output UV light when it is determined that the human is not within the area.

9. The device of claim 1, wherein the communication interface outputs the notification signal to the second controller based on at least one selected from the group consisting of: the mobile robot is unable to move because of an obstacle in the area, the mobile robot receives a selection from a user interface to request assistance, and the area is different from a map of the area used to move the mobile robot within the area.

10. The device of claim 1, wherein the at least one sensor is: an image sensor, a thermal sensor, a time-of-flight sensor, an ultrasonic sensor, a two-dimensional Light Detection and Ranging (LiDAR) sensor, a three-dimensional LiDAR sensor, and a radar (radio detection and ranging) sensor.

11. The device of claim 1, wherein at least one selected from the group consisting of: the first controller, and the second controller generates a map based on objects and surfaces detected by the at least one sensor as the mobile robot moves within the area.

12. The device of claim 11, wherein the at least one selected from the group consisting of: the first controller, and the second controller annotates the objects on the generated map.

13. The device of claim 11, wherein the generated map includes at least one from the group consisting of: rooms, doors, beds, chairs, tables, equipment, stairs, elevators, and objects in the area that are detected by the at least one sensor.

14. The device of claim 1, wherein the second controller controls the mobile robot using the at least one signal to perform at least one selected from the group consisting of: deploying the mobile robot in the area, installing the robot in the area, disinfecting the area by outputting the UV light, and controlling the mobile robot to handle an operation incident.

* * * * *